United States Patent [19]
Sultan

[11] Patent Number: 5,843,142
[45] Date of Patent: Dec. 1, 1998

[54] VOICE ACTIVATED LOCO MOTOR DEVICE AND METHOD OF USE FOR SPINAL CORD INJURIES

[76] Inventor: Hashem Sultan, 8455 Island Pines Pl., Mainville, Ohio 45039

[21] Appl. No.: 824,917

[22] Filed: Mar. 27, 1997

[51] Int. Cl.$^6$ .................................................. A61N 1/08
[52] U.S. Cl. ................................................ 607/49; 607/48
[58] Field of Search ................................ 607/48, 49, 117, 607/2

[56] References Cited

U.S. PATENT DOCUMENTS

| | | | |
|---|---|---|---|
| 4,622,973 | 11/1986 | Agarwala | 607/48 |
| 4,633,889 | 1/1987 | Talalla et al. | 607/117 |
| 4,793,353 | 12/1988 | Borkan | 607/49 |
| 4,934,368 | 6/1990 | Lynch | 607/49 |
| 5,002,053 | 3/1991 | Garcia-Rill et al. | 607/49 |
| 5,476,441 | 12/1995 | Durfee et al. | 607/49 |

OTHER PUBLICATIONS

Petrofsky, "Sequential Motor Unit Stimulation Through Peripheral Motor Nerves in the Cat," Med. & Biol. Eng. & Comput., vol. 17, pp. 87–93, Jan. 1979.

*Primary Examiner*—William E. Kamm
*Assistant Examiner*—Kennedy J. Schaetzle
*Attorney, Agent, or Firm*—Wood, Herron & Evans LLP

[57] ABSTRACT

A method and device which will enable patients with spinal cord injury to perform a variety of complex motor functions independently ( walking, sitting up or down, standing up, climbing stairs, pedaling a tricycle, exercises, etc..) by an implantable programmable device 1 which provide a coordinated stimulation to the nerve roots of the cauda equina 44. The patient will be able to activate the required function by verbally commanding the device. The command is recognized by a pre tracheal sensor 4 which relays voice vibration to the main device either wirelessly 5 or via a wire connecting the sensor to the device under the skin 7. An external programmer 24 communicates with the main device by a transmit receive circuit 26 is also provided to change the parameters of already installed data, if needed.

14 Claims, 8 Drawing Sheets

HS = HEEL-STRIKE
FF = FOOT-FLAT
HO = HEEL-OFF
TO = TOE-OFF

VOICE ACTIVATED LOCO MOTOR DEVICE AND METHOD OF USE FOR SPINAL CORD INJURIES

BACKGROUND

1. Field of Invention

The present invention relates to an implantable programmable medical device which enables patients with spinal cord injury to function independently (walking standing, etc.) on their verbal command.

The device relates generally to implantable medical devices like pacemakers, nerve stimultors, implantable device for pain management, and other implantable programmable devices used for different purposes.

1. Description of Prior Art

The idea of using electrical stimulation of muscle deprived of nervous control to produce a functionally useful movement was first described in 1961, and is known as Functional electrical stimulation "FES".

(*Arch. Phys. Med. Rehabil.*, 42, 101, 1961.)

The first application of FES to paraplegic patient was reported by Kantrwitz in 1963, using skin electrodes.

(*Electronic physiologic aids, Report of the Maimnonides Hospital*, Brooklyn, N.Y.)

Wilemon, in 1970, surgically implanted peripheral neuro-electric stimulator to stimulate both femoral & gluteal nerves.

(*Surgically implanted peripheral neuroelectric stimulation, internal report of Rancho Los Amigos Hospital*, Downey, Calif.).

An implantable multichannel FES system providing standing and swing-to and swing-through walking was developed in 1979 by Brindley et al (paraplegia, 16, 428 , 1979). Passive radio receivers were implanted together with under skin electrodes to stimulate the femoral & gluteal nerves.

Garacia-Rill et al. developed a device for inducing locomotion by electrical stimulation of the spinal cord epidurally or subdurally in animals.

U.S. Pat. No. 5,002,053. date of patent Mar., 26, 1991.

In his application he listed a number of patents and journal articles which relates to electrical stimulation in use for the treatment of pain and movement disorders, and he discussed in details the difference of those methods from his invention.

Despite the use of this device for inducing locomotion in animals by electrical stimulation of the spinal cord, this method and all other current devices are lacking fundamental principles necessary for the successful synthesis of walking or any other complex useful functions.

Other references cited:

| Patent # 5,358,514. | Date of patent: Oct. 25, 1994. |
| ☐ Patent # 4,926,865. | Date of patent: May. 22 ,1990. |
| ☐ Patent # 4,232,679. | Date of patent: Nov. 11, 1980. |
| ☐ Patent # 4,398,537. | Date of patent: Aug. 16, 1983. |
| ☐ Patent # 3,896,817. | Date of patent: July 29, 1975. |
| ☐ Patent # 5,350,414. | Date of patent: Sept. 27, 1994. |
| ☐ Patent # 4,424,812. | Date of patent: Jan. 10, 1984 |
| ☐ Patent # 5,578,063. | Date of patent: Nov. 26, 1996. |

None of the cited references described any useful clinical loco motor uses of the above devices.

This invention will enable patients with spinal cord lesion and complete or partial paralysis to perform various activities independently ( Walking, standing, sitting, standing, climbing upstairs, exercising, pedaling a tricycle, or possibly controlling bladder function, etc.).

It will also enable the above patients to change the speed of their activities by voice-activating the duration of the unit time of the function.

The main differences of this invention from the current devices and its main advantages are:

It is an implantable multichannel nerves stimulator that stimulate the nerve-roots and the Erecto-spinalis muscles and not the peripheral nerves or the spinal cord.

It is a programmable functional electrical stimulator (FES) that induce a wide variety of useful functions on patient's command.

The motor function is achieved by a coordinated selection of the nerve-root to be stimulated and by changing the current intensity of the stimulation over a time unit ($dI/dT$) so that a predictable myo-electrical response is obtained , which in turn leads to the desired motor function.

Program instructions of the required functions can be pre-installed in the memory of the implantable device (Main device).

For special cases an external programmer can be used to adjust the parameters (current intensity, duration, nerve-root selection) required for that particular case. These data can then be transmitted to the implantable device for storage .

Communication between the implantable device and the external programmer can be achieved using radio frequency, infrared or ultrasound or any other means of telecommunications.

The device is activated by patient's verbal command . A sensor is implanted opposite the trachea under the skin. The vibrations of the patient's voice are transmitted to the main device by a transmitting circuit implanted close to the sensor, or carried by a wire tunneled under the skin and connecting the sensor to the main device.

The invention will enable patients with spinal cord injury to perform various activities independently ( walking, sitting down, standing up, climbing stairs, pedaling a tricycle, etc.).

By mobilization, complications of SCI will be greatly reduced . These complications include bedsores, deep venous thrombosis, pulmonary emboli, recurrent chest infections, recurrent urinary tract infections, contractures, osteoporosis, depression, etc.

The invention will open a new era in the treatment and rehabilitation of spinal cord injured patients, and gives these patients a realistic hope to return to a near normal functioning life.

save the national resources.

The direct medical costs of the SCI to the federal government exceeds $4 billion per year. With current traditional medical and physical care the lifetime costs is estimated to be greater than $1 million per individual. There are approximately 11,000 new patients with SCI each year added to the national pool.

The current device is expected to reduce tremendously medical costs by preventing the usual complications in SCI patients and by changing the needs for continuous passive rehabilitation programs.

REFERENCE NUMERALS IN DRAWINGS

Figure 1B:
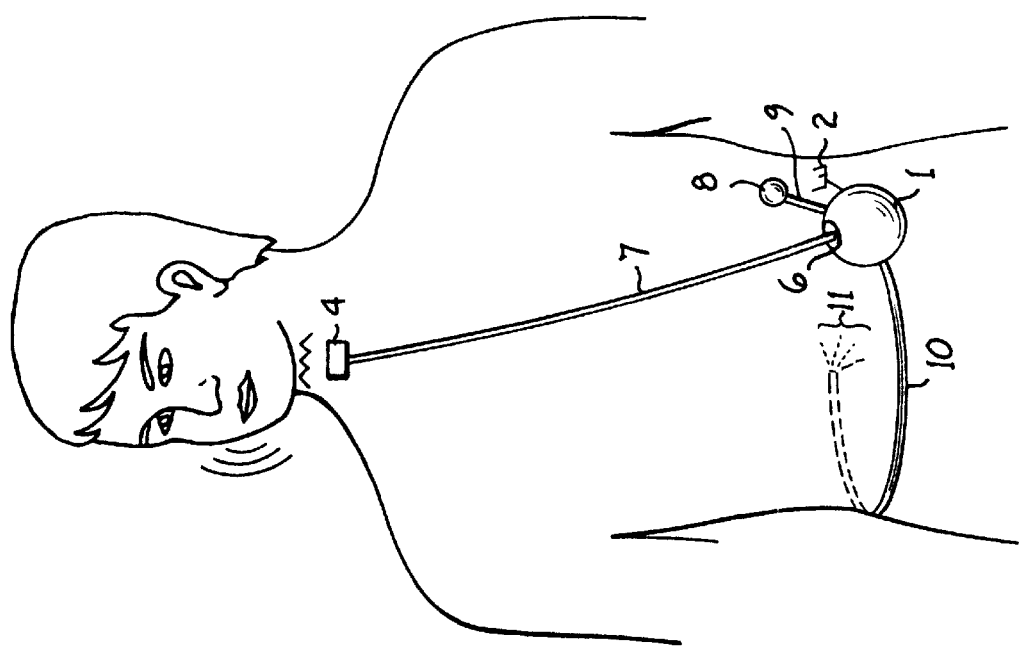
FIG. 1B is an illustration of one embodiment of the invention in a human where the implantable programmable device communicates with the main device by a connector wire under the skin."

1 Implantable programmable unit (main device).
2 Antenna, to receive transmission from the external programmer.
3 Antenna, to receive transmission from the pre tracheal transmitter.
4 Pre tracheal voice vibration sensor.
5 Pre tracheal transmitting unit.
6 Voice vibrations signal receiver.
7 A wire connecting the pre tracheal sensor to the main device.
8 power supply.
9 wires connecting the power supply to the main device.
10 Cable of fine electrodes.
11 Bundle of labeled or color-coded fine electrodes.
12 Connector between the voice signal receiver and the wire 7.
13 A transmit—receive circuit for communication with the external programmer.
14 Decoder: A/D converter.
15 Decoder: A/D, D/A converter.
16 Microprocessor controller.
17 Memory of pre-installed programs and storage for new data.
18 Multiplexor.
19 Latches.
20 Transducers.
21 resistors.
22 Stimulation output to right nerve roots.
23 Stimulation output to left nerve roots.
24 External programmer.
25 Antenna of the external programmer.
26 A transmit-receive circuit.
27 Memory.
28 A/D, D/A converter.
29 key board for selecting the function.
30 Key board for changing the duration of the time unit.
31 Key board for selecting the intensity of the current.
32 Key board for selecting the nerve root to be stimulated.
33 "enter" key to enter the accepted parameter.
34 "LCD" display.
35 A key to move choices downward.
36 A key to move choices upward.
37 power supply to the external programmer.
38 Connector of the main device to fine electrodes cable (10).
39 Connector of fine electrodes cable to the main device.
40 connection between fine electrodes cables.
41 A second fine electrodes cable.
42 A fine electrode.
43 Non-insulated terminal of the fine electrode.
44 A nerve root.
45 Insulating adhesive piece.
46 On-off switch.
47 Key board for selecting final pathway of the new parameters.

III-SUMMARY

It is an object of the present invention to provide a method and device which will enable patients with a spinal cord injury to function independently.

It is a totally new idea of using the nerve-roots themselves to achieve complex motor activities and overcome the disadvantages of the prior arts.

The main object of the present invention is to coordinate the intensity and duration of the nerve roots electrical stimulation by a programmable controller so that a desirable muscle function is achieved which when coordinated with the stimulation of the other muscle groups will lead to the desired motor function.

The selection of the nerve root to be stimulated and the duration and intensity of the stimulation can be incurred from studies on the timing of muscles activities and EMG (electromyography) information during walking, and other activities.

According to the present invention the best site for electrode placement is the level of the nerve roots themselves at the cauda equina level where the whole nerve roots on both sides can be approached by a single laminectomy procedure.

Each nerve root can be identified intra operatively using the traditional nerve stimulator. A labeled or colour-coded electrode is then hooked to the corresponding nerve-root, and the electrode cable is tunneled under the skin to be attached to the implantable unit.

The implantable unit is then placed under the skin of the abdominal wall. The tunneled electrode cable is then plugged into this unit The power supply of the unit can be either embedded in the unit or can be implanted under the skin in a different site and then connected to the unit by tunneled cable under the skin. This option has the advantage of changing the battery without disturbing the whole unit.

An external programmer is used to modify the parameters already installed in the memory of the main device. It communicates with the main device by a two-way communication circuit which uses radio frequency, infra red, ultrasound, or any other means of telecommunication.

The main device is activated by patient's verbal command. A vibration sensor is implanted under the skin opposite the trachea (pre tracheal). The vibration signals are transmitted to the main device either wirelessly using a transmitting circuit implanted close to the sensor, or via a wire tunneled under the skin.

Physiological Basis of the Idea

The spinal cord is an elongated cylindric mass of nerve tissue which occupies the upper two-thirds of the vertebral canal (Spine). It extends from the brain stem to the upper border of the second lumbar vertebra. Thirty-one pairs of spinal nerves arise from the spinal cord. The collection of the Lumbo-sacral nerve roots is referred to as the Cauda Equina (5 lumbar & 5 Sacral).

These ten pairs of the spinal nerves are responsible for the motor and sensory function of the lower limbs. They are anatomically and functionally intact in spinal cord injured patients. However, the patient's ability to control their function is lost as a result of interruption of the connection between the brain and those nerve roots. The muscles innervated by these nerves are also intact. Therefore, what is required to restore a normal function is the coordinated stimulation of these nerves to achieve the required functions.

The following facts need to be emphasized:

Despite the fact that each muscle group is innervated by 2 to 4 nerve roots, usually one nerve root is the most important in the function of that muscle group (example L5 root in ankle dorsiflexion and S1 root in ankle plantar flexion).

By innervating agonist and antagonist muscle group by the same nerve root the net effect on joint function is negligible (Example: L4 root on hip adductors and hip abductors).

By stimulating the primary nerve root of agonist group muscles a maximal contraction may be reached by conducting the nerve stimulation retrogradely into the secondary nerve roots.

The primary nerve root for the agonist muscles are:
1. Hip flexion: L1, L2.
2. Hip extension: L5, S1.
3. Hip adduction: L3
4. Hip abduction: L5
5. Knee extension: L3
6. Knee flexion: L5, S1.
7. Ankle dorsi-flexion: L5
8. Ankle Plantar-flexion: S1, S2.

Stimulation of L4 only will partially stimulate all muscle groups agonists and antagonists and therefore has minimal functional result.

Stimulation of L3, L4 and L5 at the same time produce mainly hip and knee extension, with ankle dorsiflexion.

Stimulation of S1 & S2 will produce hip extension, knee flexion and ankle plantar-flexion.

Programming any function should be based on the above understanding of the primary nerve root of the agonist and kinematics of that function.

Figure 8A:
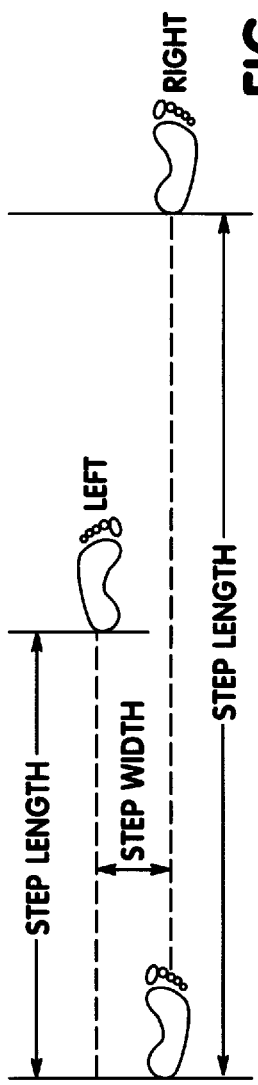
FIGS. 8A, 8B, and 8C: Phases of the gait cycle are shown on the same time-axis for the left and the right leg.
Figure 8B:
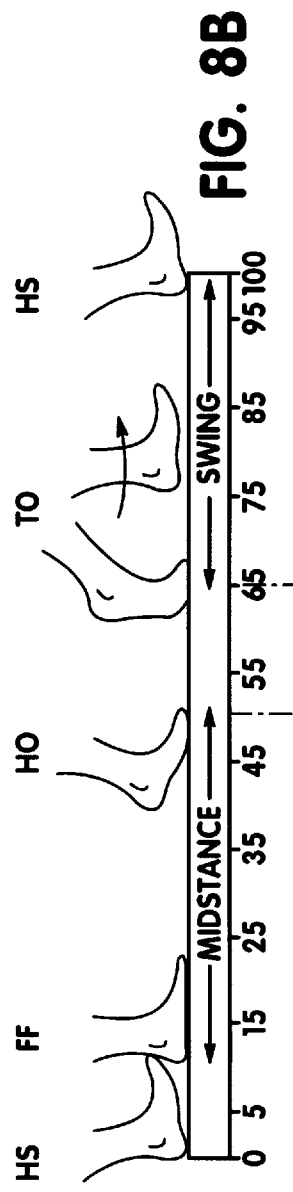
Figure 8C:
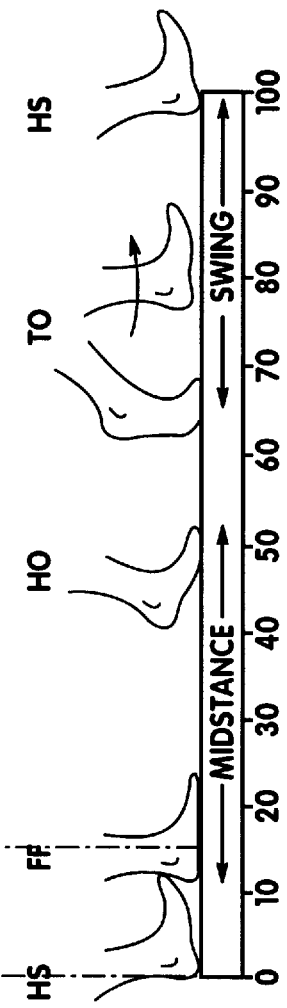

The following is an example of programming walking:

During a walking cycle, a given foot is either in contact with the ground (Stance phase of the gait cycle) or in the air (swing phase). The duration of the gait cycle for any one limb extends from the time the heal contacts the ground (called heel-strike or heel-on) until the same heel contacts the ground again as illustrated in FIGS. 8A, 8B, and 8C of the enclosed copy.

The stance phase begins with initial contact of the foot (usually heel-strike) and ends with the foot leaving the ground (called Toe-off).

The swing phase begins with toe-off and ends with heel-strike.

At ordinary walking speed, the stance phase occupies approximately 60% and the swing phase 40% of a single gait cycle.

A typical cycle can be expected to last 1 to 2 seconds, depending on walking speed.

FIGS. 8A, 8B, and 8C of the enclosed rough drawing shows that a period of double support exists when both limbs are in a stance phase. This period varies inversely with the speed of walking.

Each of the primary phases of the gait cycle can be subdivided into various stages called the sub-phases of the gait. For example, the stance phase is comprised of HS (heel-strike), FF (flat-foot), HO (heel-off and TO (toe-off) sub-phases.

Figure 7:
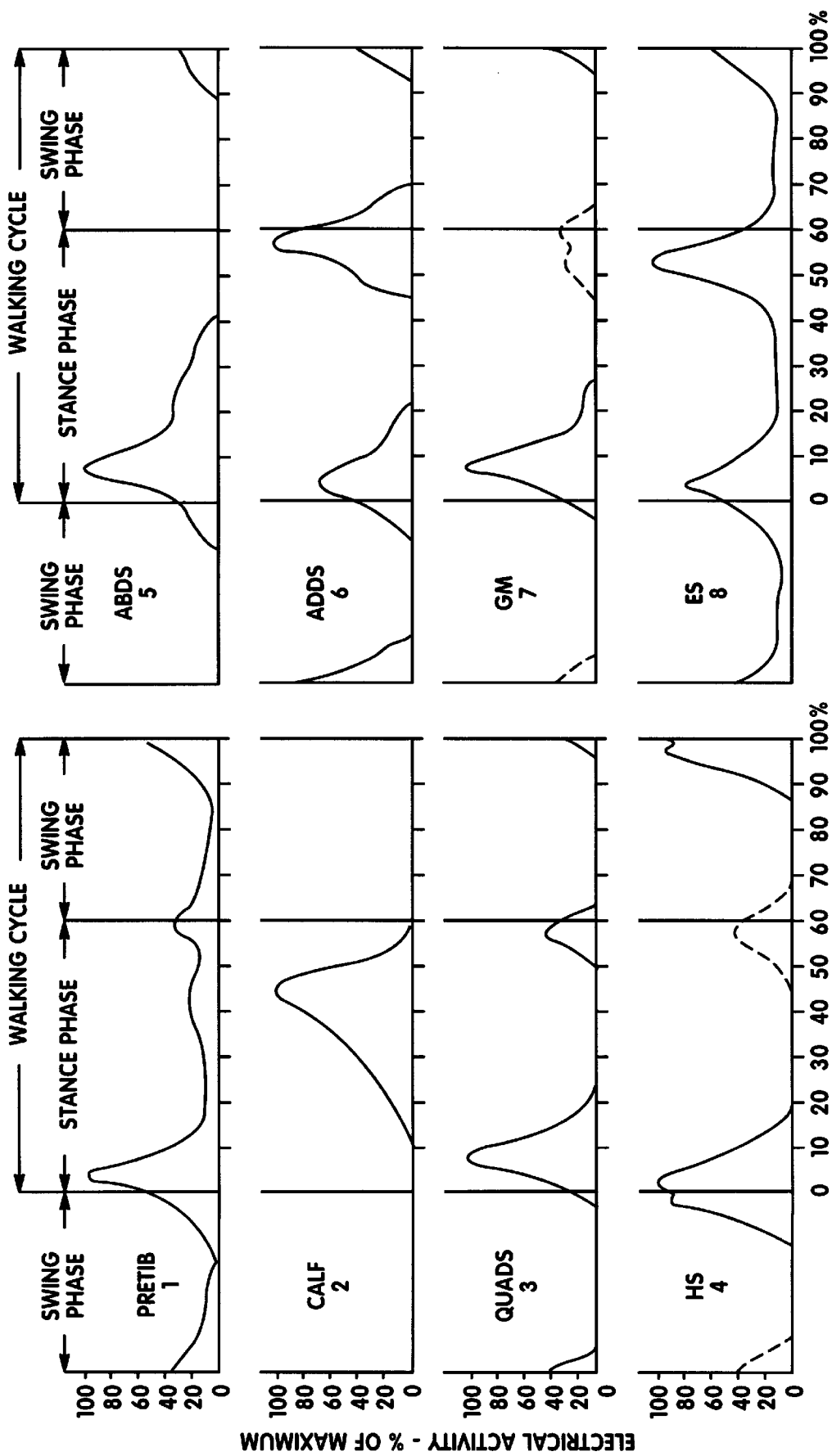
FIG. 7: Idealized summary curves representing phasic actions of the major muscle groups in level walking at 90 steps/min in normal individuals.

FIG. 7 of the enclosed rough drawing shows a summary of curves representing phasic action of the major muscle groups in level walking at 90 steps/min.

Figure 9:
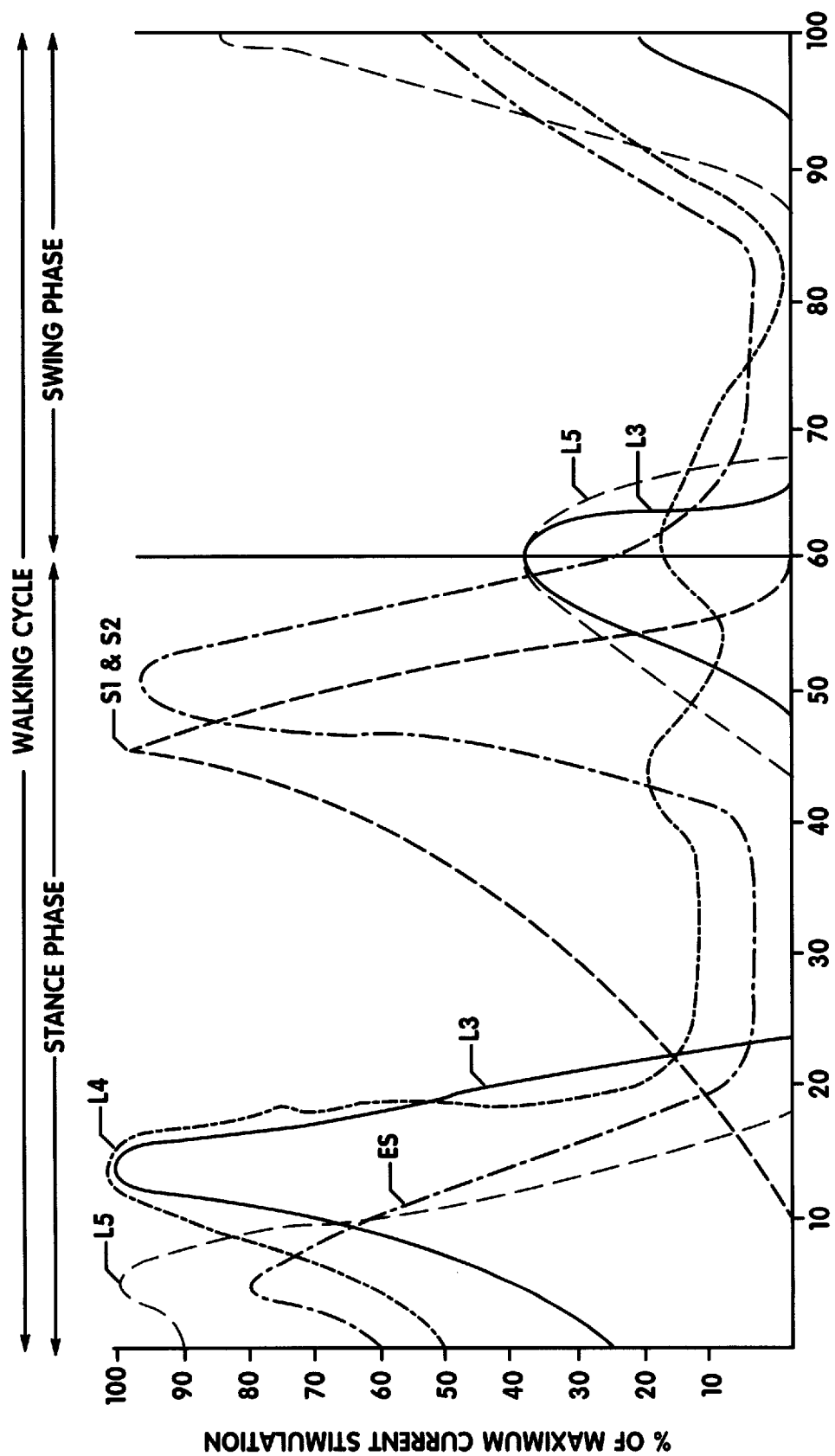
FIG. 9: Phasic stimulation program of the nerve-roots of one leg for walking activity.

FIG. 9 of the enclosed rough drawing shows the corresponding nerve root stimulation in regard to intensity and duration during this phasic cycle.

Changing the speed of the walking requires only changing the preset time unit of the gait cycle.

All other functions (like stopping, standing, sitting, climbing stairs, pedaling, exercises of certain group of muscles, etc..) can be programmed easily based on the above facts and the understanding of the kinematics of that function.

IV. DETAILED DESCRIPTION OF THE PREFERRED EMBODIMENTS AND OPERATION

The present invention relates to a method and device for inducing complex motor activities in patients with a spinal cord injury on their verbal commands, so that the patient will be able to walk around and do their own physiotherapy independently.

The patient with a spinal cord injury has intact nerves and muscles anatomically and functionally in the lower limbs, but his ability to control their function is lost as a result of interruption of the connection between the brain and those nerve roots. Therefore, a coordinated stimulation of these nerve roots using the current invention will produce the required function.

FIG. 1B shows the general assembly of the device. The main unit 1 is placed under the skin of the abdominal wall. Its power supply 8 can be either embedded in the main unit or preferably implanted separately under the skin at a different site, so that, changing the power supply, if needed, will not disturb the whole device and reduces the risk of infection. The power supply is a rechargeable battery that can be recharged externally. Connection of the power supply to the main device is via an implantable cable 9 tunneled under the skin.

Figure 1A:
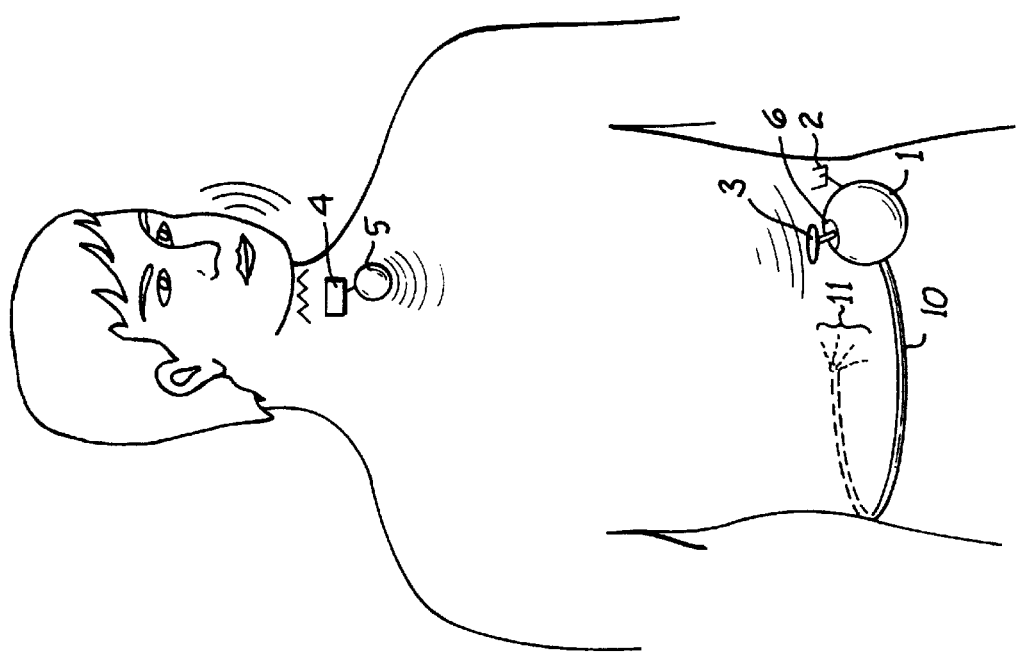
"FIG. 1A is an illustration of one embodiment of the invention in a human where the implantable programmable device communicates wirelessly with the main device via an implantable pretracheal transmitter.

A pre tracheal sensor 4 is implanted under the skin adjacent to the trachea. This sensor senses the vibration produced by the patient'verbal command. The signal of this command is carried to the main device via a tunneled conducting wire 7 This wire is connected to the main unit by an appropriate connector 12 shown in FIG. 2. The signals can also be transmitted wirelessly using an implantable transmitting unit 5 placed adjacent to the sensor 4 in the pre tracheal area (see FIG. 1A). This transmitting unit communicates with the main device by a compatible receiver 6 embedded in the main device (FIG. 2).

Each of the above mentioned units (power supply 8, pre tracheal transmitting unit 5, and the main device 1) is contained in a special envelope which can be of any non-corrosive material and in any shape.

Figure 2:
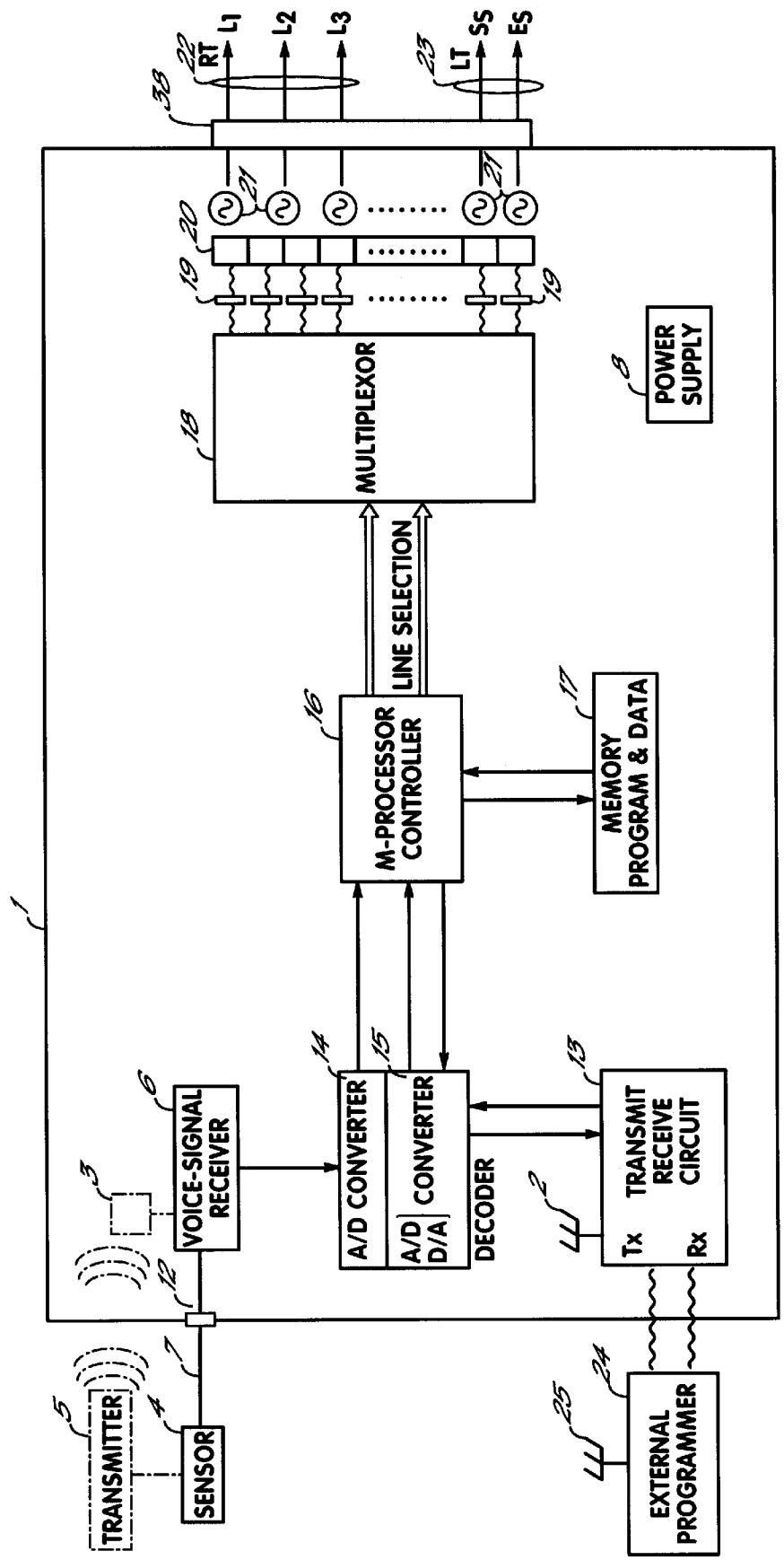
FIG. 2: Schematic drawing of the circuits that comprises the main device
Figure 3:
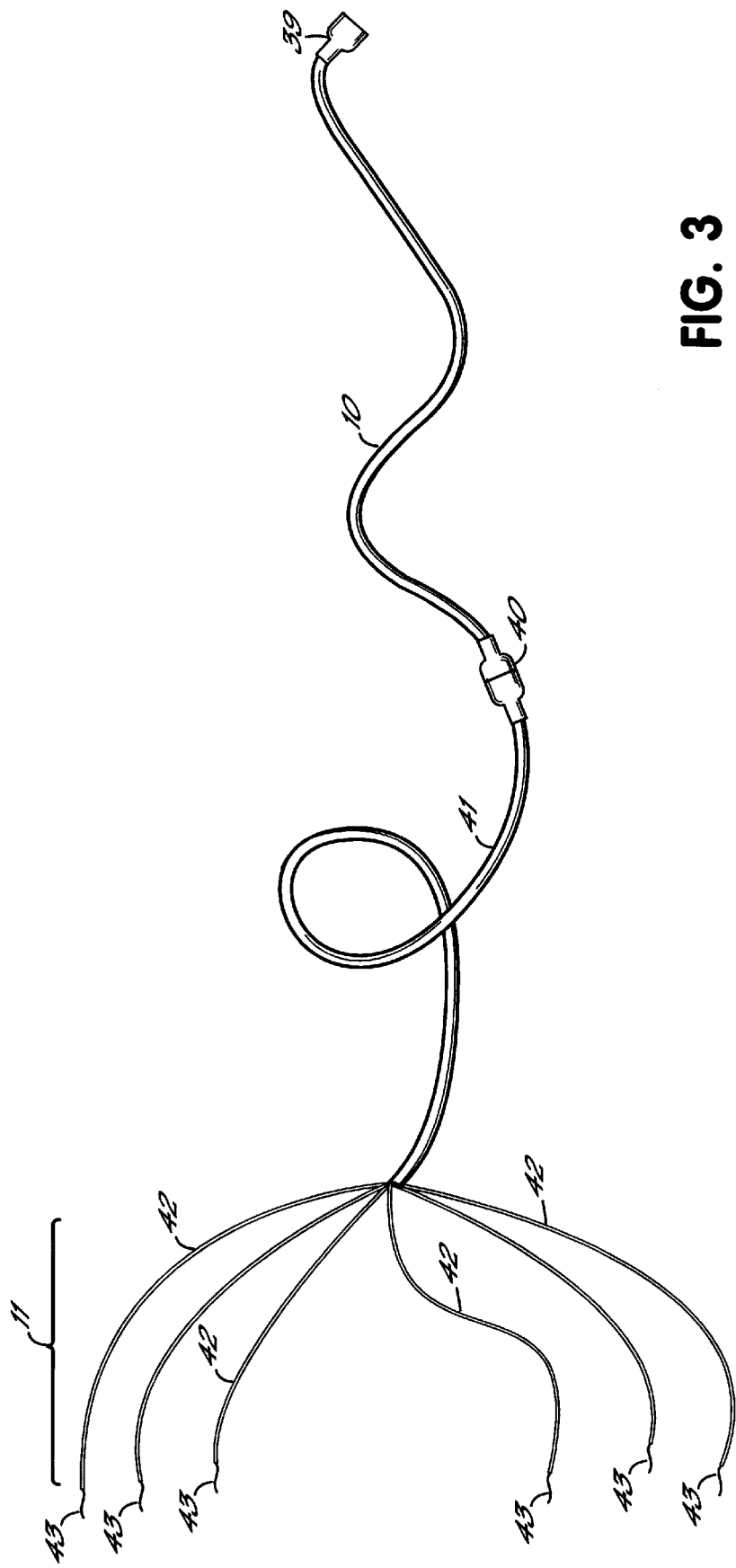
FIG. 3: Illustration of the fine labeled or colour-coded electrodes bundle.

FIG. 2 shows the rough drawing of the circuits that comprise the main device 1. A voice signal receiver 6 receives the voice vibration signals either via wire 7 which carries the signals directly from the sensor 4 or wirelessly via an antenna 3 embedded in the main device which receives the signal from the pre tracheal transmitter 5. The signal is then converted to digital information by an A/D converter 14. This converter relays the digitized signals to a microprocessor controller 16.

The microprocessor 16 realizes the function already ordered and reads the data stored in the memory 17 and relays the information to a multiplexor 18. The information relayed will be the parameters of nerve root selection, the current intensity, and the duration.

The multiplexor distributes the relayed information to each port which corresponds to a particular nerve root. The parameters of these information to each nerve root are the current intensity changes over a time unit (DI/dT). Transducers 20 will convert these parameters into current stimulation which changes in time in response to the multiplexor data. Latches 19 may be placed in between the multiplexor and the transducers. The current will pass through resisters 21 to modify its intensity to the required changes. The current output is delivered separately to each port which corresponds to a particular nerve root.

The output ports are grouped in one connector 38 (FIG. 2, and FIG. 4) to which the cable of the fine electrodes 10 is connected.

The microprocessor 16 also interacts with a transmit-receive circuit 13 and its two-way converter 15 to store new information transmitted from the external programmer 24. This two-way communication module uses radio frequency, infra red, ultrasound signals or any other methods of telecommunication. It can also transmit the information already stored in the memory of the main device to the external programmer for verification.

Figure 4:
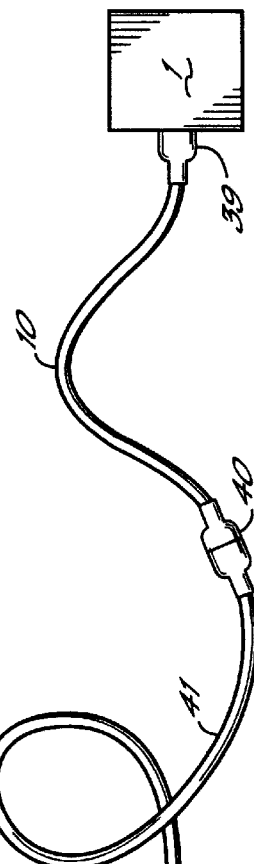
FIG. 4: Illustration of the positions of the fine electrodes on the cauda equina in the spinal canal.
Figure 4:
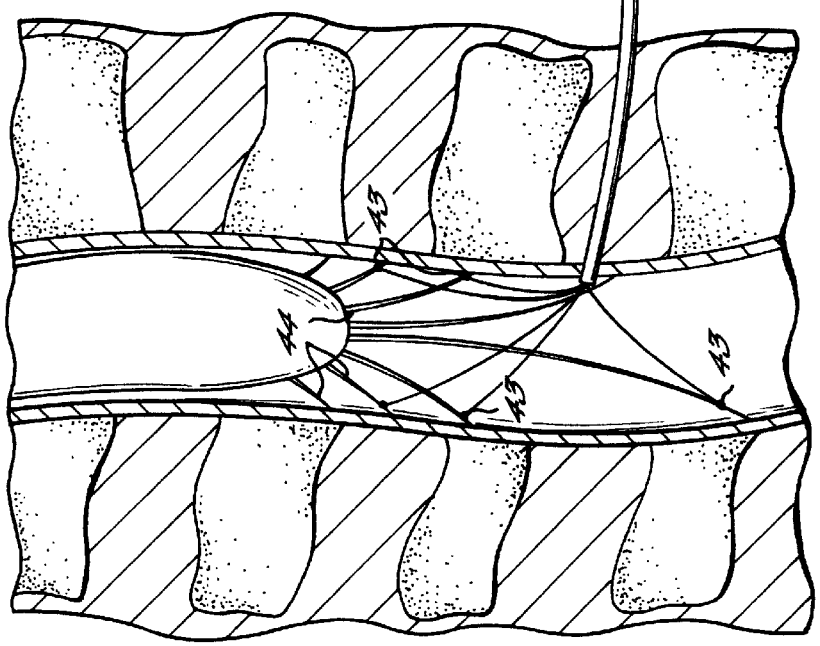

The stimulation of the main device is carried to the nerve roots via cables 10 & 41 FIG. 1 and FIG. 4, connected by appropriate connector 40. These cables contain a bundle of fine electrodes 11

Each of these fine electrode 42 is either coded or color-specific to a certain nerve root. The proximal end of cable 10 has a compatible plug to port 38 of the main device.

Figure 5:
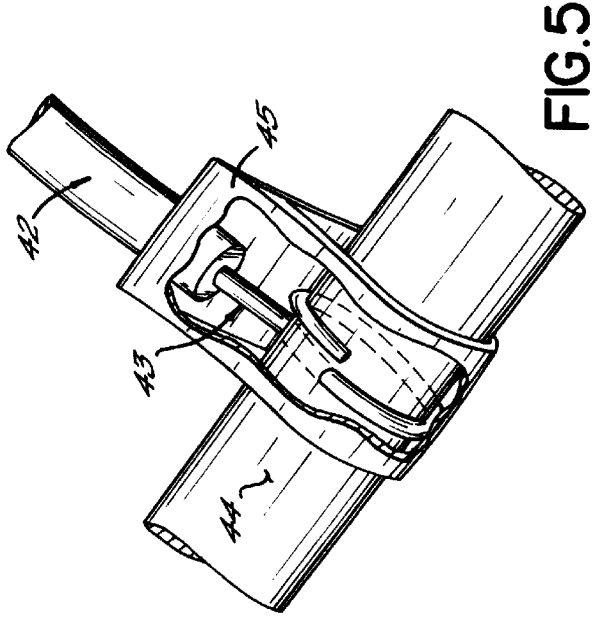
FIG. 5: Illustration of the preferred method of attaching the fine electrodes to the nerve-root.

The distal end 43 of the fine electrodes are non-insulated and are to be hooked to a specific nerve root 44 (FIG. 4 and FIG. 5). FIG. 5 shows the preferred method of hooking the fine electrode to the nerve root.

The attachment of the fine electrode to the nerve root can be made of many other different ways and not necessarily a hooking mechanism (a clamp for instance).

An insulated adhesive piece 45 is wrapped around the attachment of the fine electrode to the nerve root to prevent dissemination of the stimulation current in the CSF (cerebro spinal fluid). This piece can be made of any available material like patty, cottonoid, etc..

The cables 10 and 41 can be made as one cable with one end being plug 39 and the other end the fine electrode bundles 11. However, the main advantage of using two cables is in case of infection. This will enable us to remove the infected part(s) without the need to approach the spine. After the infection is cleared the device can be installed easily by abdominal approach only.

Figure 6:
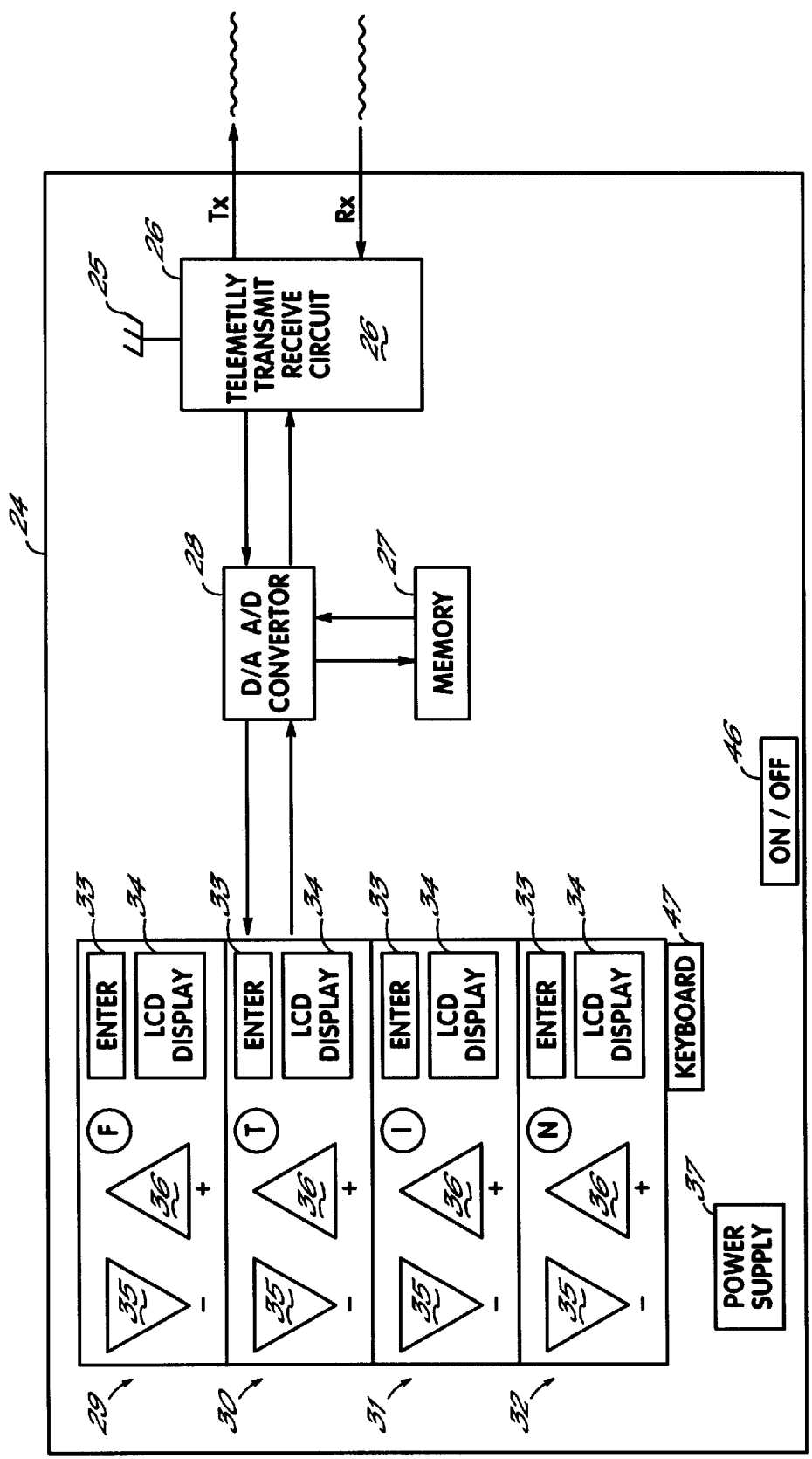
FIG. 6: A schematic drawing of the external programmer.

FIG. 6 is a rough drawing of the external programmer 24. This device will be used to make the necessary changes in the parameters already installed and to verify data stored if any problem arises.

It comprises multiple key boards to activate the functions.

Key board 29 is for selecting the function to be modified (walking, climbing, etc . . . ).

Key board 30 is for modifying the time unit of the function and therefor the speed of performing the action.

Key board 31 is for changing the current intensity of a chosen nerve root or function. Key board 32 is for choosing the nerve root whose parameters need to be changed.

Keys 35, 36 move upward or downward in the selection list. Key 33 enters the chosen parameter. LCD display 34 shows the parameter selected.

Key board 47 enters the new parameters in the memory of the external controller or transmits these new data to the implantable device for testing or for storage in the memory.

The external controller comprises the necessary circuits well known to ordinary people in the art of electronics. Some of the necessary circuits are DIA, A/D converter 28, memory 27, transmit-receive circuit 26 communicating with the transmit-receive circuit of the main device 13.

FIG. 7 shows the idealized summary curves representing phasic action of the major muscle groups in the lower extremity in level walking at 90 steps/min. The amount of electrical activities recorded from the muscle group is expressed as a percentage of the maximum electric activity recorded from the group while walking. It is not the maximum amount of activity that the particular muscle group is capable of producing with a maximum contraction.

FIG. 8 Shows the phases of the gait cycle on the same time axis for the left and right leg.

(A) Representation of the stride dimensions as viewed from beneath the subject.

(B) Side view of one complete cycle of the right leg (C) Side view of one complete cycle of the left leg.

The time axis indicates the percentage of the gait cycle completed, starting and ending with HS (heel-strike). Note that two steps occur during each stride. Also note that a period of double support exists when both limbs are in a stance phase.

FIG. 9 is a diagram of the phasic stimulation of the nerve roots to achieve the same EMG (muscle action potentials) in FIG. 7 and the sub phases of the gait cycle shown in FIG. 8B.

The maximal current stimulation for each nerve root will vary from one nerve root to another.

L3, L4, L5 (Lumbar nerve root #3, #4, #5 )

S1, S2 (Sacral nerve root #1, 2.)

ES (Erecto spinalis muscle)

The device should generally have at least 14 electrodes, preferably 22 electrodes (5 right and 5 left lumbar, 5 right and 5 left sacral, and one on each side for the erecto-spinalis muscle).

Although the description above contains many specifies, these should not be constructed as limiting the scope of the invention but as merely providing illustrations of some of the presently preferred embodiments of this invention. For example, the non-insulated end of the fine electrode can be of different shape and design for attachment to the nerve root. The transducers 21 in FIG. 5 could be one unit with multi transducers.

Thus the scope of the invention should be determined by the appended claims and their legal equivalents, rather than by the examples given.

I claim:

1. A system for inducing complex motor functions in a person comprising:

a sensor operable for detecting a vocal command from a person and generating a command signal corresponding to said vocal command;

a controller operably coupled to said sensor, said controller operable for receiving the command signal and generating a control data sequence related to the command signal;

a plurality of transducers coupled to the controller for receiving and converting the control data sequence into a sequence of stimulation signals for stimulating nerve roots, the stimulation signals of the sequence including specific stimulation parameters;

a plurality of individual electrodes coupled to said transducers, each electrode configured for being implanted beneath the skin of the person and coupled to an individual nerve root in the spinal cord;

the transducers producing the sequence of stimulation signals for selectively exciting individual nerve roots in a sequence and according to specific stimulation parameters of the stimulation signals for producing a desired motor function.

2. The system of claim 1 further comprising a programming circuit coupled to the controller, the programming circuit operable for modifying the control data that is generated by said controller in response to said command signal to thereby modify the motor function produced by the system.

3. The system of claim 1 wherein said control data is stored in memory, the controller accessing said memory to generate the control data in response to said command signal.

4. The system of claim 1 wherein said control data includes variable parameters, the variable parameters determining the stimulation parameters of the stimulation signals.

5. The system of claim 1 wherein said stimulation signal parameters include at least one of the group of signal duration and signal intensity.

6. The system of claim 1 further comprising a multiplexing device coupled between said controller and said transducers for selectively directing control data of the sequence to individual transducers of said plurality for producing the stimulation signal sequence.

7. The system of claim 1 wherein said vocal sensor comprises a transmitting unit configured for mounting proximate the trachea of a person to generate the command signal, and a receiving unit coupled to the controller and remote from said transmitting unit, for wirelessly transmitting said command signal to the controller.

8. The system of claim 2 wherein said programming circuit comprises a keyboard to receive user inputs for modifying the control data that is generated by said controller in response to said command signal.

9. A method for inducing complex motor functions in a person comprising:

detecting a vocal command from a person and generating a command signal corresponding to said vocal command;

receiving the command signal with a controller and generating a control data sequence related to the command signal;

converting the control data sequence into a sequence of stimulation signals for stimulating individual nerve roots, the stimulation signals including specific stimulation parameters;

coupling individual electrodes to individual nerve roots in the spinal cord and delivering the stimulation signals in the sequence to the individual nerve roots through the electrodes for selectively exciting the nerve roots to produce a desired motor function.

10. The method of claim 9 further comprising programming the controller for modifying the control data sequence generated by said controller in response to said command signal to thereby modify the motor function produced by the system.

11. The method of claim 9 wherein said control data is stored in memory, the method further comprising accessing said memory to generate the control data in response to said command signal.

12. The method of claim 9 wherein said control data includes variable parameters, the variable parameters determining the stimulation parameters of the stimulation signals.

13. The method of claim 9 wherein said stimulation signal parameters include at least one of the group of signal duration and signal intensity.

14. The method of claim 9 further comprising detecting said vocal command with a transmitting unit mounted proximate the trachea of a person and generating the command signal, wirelessly transmitting said command signal to a receiving unit coupled to the controller and remote from said transmitting unit.

* * * * *